United States Patent [19]
Zighelboim R

[11] Patent Number: 5,366,732
[45] Date of Patent: Nov. 22, 1994

[54] METHOD OF MILKING COWS

[76] Inventor: Jaime Zighelboim R, 20281 E. Country Club Dr., Apt. #1107, Aventura, Fla. 33180

[21] Appl. No.: 229,144

[22] Filed: Apr. 18, 1994

Related U.S. Application Data

[63] Continuation of Ser. No. 50,523, Apr. 20, 1993, abandoned, which is a continuation-in-part of Ser. No. 529,888, May 29, 1990, abandoned.

[51] Int. Cl.$^5$ .............................................. A61K 9/70
[52] U.S. Cl. ................................... 424/411; 424/402; 424/405; 424/414; 119/158
[58] Field of Search ............... 424/411, 402, 405, 414; 119/158

[56] References Cited

U.S. PATENT DOCUMENTS

| | | | |
|---|---|---|---|
| 3,713,423 | 1/1973 | Sparr, Sr. ........................... | 119/158 |
| 3,857,934 | 12/1974 | Bernstein et al. .................... | 429/411 |
| 4,045,364 | 8/1977 | Richter ................................. | 424/411 |
| 4,199,564 | 4/1980 | Silver et al. ......................... | 426/411 |
| 4,288,428 | 9/1981 | Föll et al. ........................... | 424/78.02 |
| 4,305,346 | 12/1981 | Sparr, Sr. ........................... | 119/158 |
| 4,472,374 | 9/1989 | Dowrick et al. ................... | 424/78.02 |
| 4,847,089 | 7/1989 | Kramer et al. ...................... | 424/411 |
| 4,888,175 | 12/1989 | Burton, Jr. et al. ................ | 424/411 |

OTHER PUBLICATIONS

Budavari et al. (1989). The Merck & Co., Inc., "The Merck Index", p. 1072.

*Primary Examiner*—G. S. Kishore
*Assistant Examiner*—Raj Bawa
*Attorney, Agent, or Firm*—Ralph Bailey

[57] ABSTRACT

A method of preparing, treating and then milking cows includes the use of a flexible wipe (A) constructed of hydrophilic material containing a moisture-activated antimicrobial composition. The process includes washing teats and udder of a milk-bearing cow with water or an aqueous soap solution; simultaneously drying, sanitizing and conditioning the thus-washed teats and udder with the moisture-activated antimicrobial wipe comprising a hydrophilic substrate impregnated with an antimicrobial agent, effective to sanitize the teats and udder; and then milking the thus-prepared cow.

7 Claims, 2 Drawing Sheets

METHOD OF MILKING COWS

This application is a continuation of U.S. Ser. No. 08/050,523 entitled METHOD OF MILKING COWS, filed Apr. 20, 1993, now abandoned which is a continuation-in-part of U.S. Ser. No. 07/529,888 entitled METHOD OF MILKING COWS, filed May 29, 1990, which is now abandoned.

TECHNICAL FIELD

This invention relates to an improved process for milking cows, more particularly to the provision of a process for simultaneously drying, sanitizing and conditioning teats and udder of a milk-bearing cow and thereafter milking the thus-prepared cow. Background Art The prior art generally teaches the application of various udder disinfectants as by washing or dipping before or after milking to prevent infection. Special apparatus has been provided for washing and cleansing the teats of a cow preparatory to milking as illustrated in U.S. Pat. No. 3,713,423 wherein a disinfectant solution is applied in a cup successively to the teats. Apparatus for simultaneously washing and stimulating the teats is illustrated in U.S. Pat. No. 4,305,346. Such apparatus is expensive and difficult to use leaving the teats wet. Moreover, such apparatus is difficult to decontaminate after each use so that the use of such apparatus in successive milking operations risks infecting other cows.

In dairy farming it is conventional to spray or dip the teats and udder of a cow with sanitizer or soap solution before milking the cow. The teats are then dried, often in two separate steps by two different workers, as proposed by Braum (U.S. Pat. No. 4,763,605). A third step, requiring a third worker, is testing the milk from each teat by manually squirting a small sample of milk from each teat into a separate container. A fourth worker attaches the teat cups to the teats, connects the teat cups to a vacuum source and begins the milking action. At the end of the milking process, the teat cups are disconnected and the teats and udder are sterilized with an antiseptic spray.

Shakarian (U.S. Pat. No. 3,301,215) has proposed a method for milking cows in which the cows are washed in one area, dried in a second area and conditioned for milking in a third area by directing a warm gaseous stream at the udders. It has been found that, without conditioning the cow to let down the milk in some fashion, milk output is significantly less than potentially available. Foll et al. (U.S. Pat. No. 4,288,428) have proposed disinfecting teats and udder with an emollient iodophor composition, in the form of a dip.

The unrelated use of substrates impregnated with antimicrobial or sterilizing agents are disclosed, for example, by Henry (U.S. Pat. No. 1,353,954), Morin (U.S. Pat. No. 2,837,462), Scheuer (U.S. Pat. No. 3,227,614) and Hinz (U.S. Pat. No. 3,728,213), herein incorporated by reference. Impregnation of substrates with an antimicrobial agent and a detergent has been proposed by Hein et al. (U.S. Pat. No. 3,138,533), Decker et al. (U.S. Pat. No. 3,283,357) and Richter (U.S. Pat. No. 4,045,364). Other microbicide-impregnated wipers are disclosed by Gresham (U.S. Pat. No. 3,264,188), Scheuer (U.S. Pat. No. 3,619,280), Buchalter (U.S. Pat. No. 3,896,807), Eggensperger et al. (U.S. Pat. No. 4,259,383) and Rothe et al. (U.S. Pat. No. 4,738,847). Demner has proposed, in U.S. Pat. No. 3,496,589, using a foam saturated with insecticidal shampoo for treating dogs. Inclusion of germicides in textile-conditioning dryer sheets has been proposed by McQueary (U.S. Pat. No. 4,007,300) and Siu et al. (U.S. Pat. No. 4,177,151).

SUMMARY OF THE INVENTION

It is an object of this invention to simplify milking of cows by using a disposable water-activated or water-activatable antimicrobial wipe to simultaneously dry, sanitize and condition the teats and udders of milk-bearing cows, immediately prior to milking them.

Another important object of this invention is to prepare cows for milking while treating the teats to reduce contamination of the milk collected, including cleansing the teats of a milk-bearing cow by washing and applying an aqueous liquid thereto so as to leave the teats wet therewith.

Another important object of the invention is to manually massage the teats while the teats are still wet with a flexible wipe constructed of hydrophilic material containing a moisture-activated antimicrobial composition releasable from the wipe by uptake of water from an aqueous liquid from the wet teats and moistening the wipe as a result of the massaging, and continuing to manually massage the teats with the wipe after moistening thereof so as to apply the moisture-activated antimicrobial composition released from the wipe to the teats disinfecting them while stimulating them for enhanced milk production through massage. By discarding the flexible wipe prior to preparing and treating another cow to avoid the possibility of infecting another cow and then milking the thus-prepared cow, washing and drying of the teats of a cow are accomplished in such a way as to prepare the cow for milking while disinfecting the teats to avoid contamination of the milk produced and to increase the amount of milk produced during milking.

BRIEF DESCRIPTION OF THE DRAWINGS

The construction designed to carry out the invention will be hereinafter described, together with other features thereof.

The invention will be more readily understood from a reading of the following specification and by reference to the accompanying drawings forming a part thereof, wherein an example of the invention is shown and wherein:

FIG. 2 is an enlarged perspective view of the non-woven fabric of the wipe;

DISCLOSURE OF INVENTION

Figure 1:
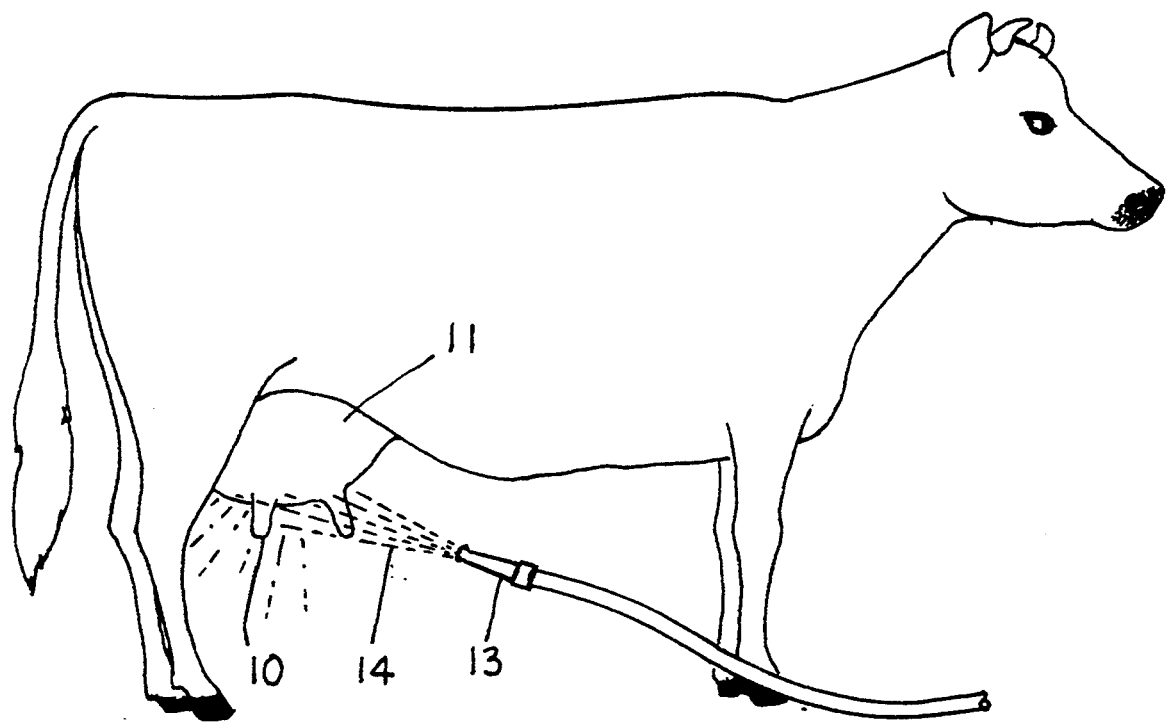
FIG. 1 is a perspective view illustrating the washing of the teats and udder of a cow with soapy water.
Figure 2A:
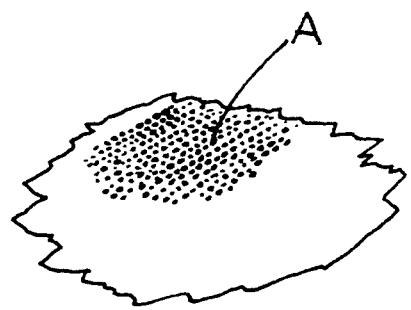
FIG. 2 is a perspective view illustrating a non-woven wipe impregnated with a water-activated antimicrobial composition.
Figure 2:
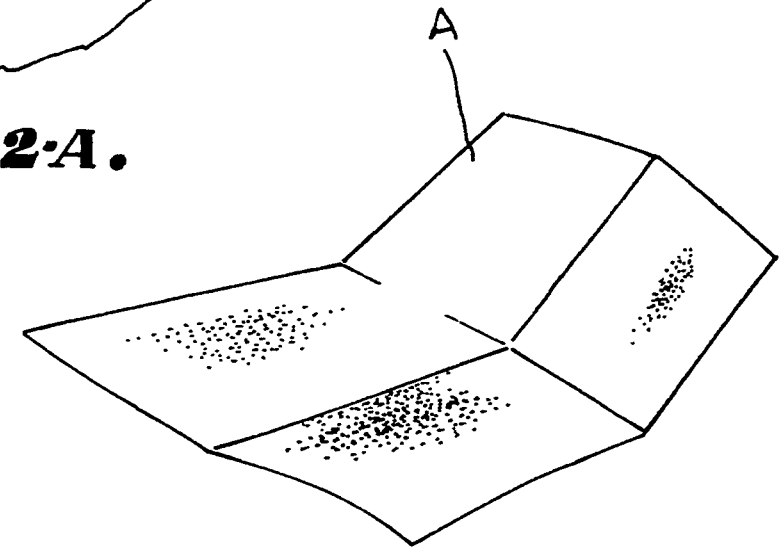
Figure 3:
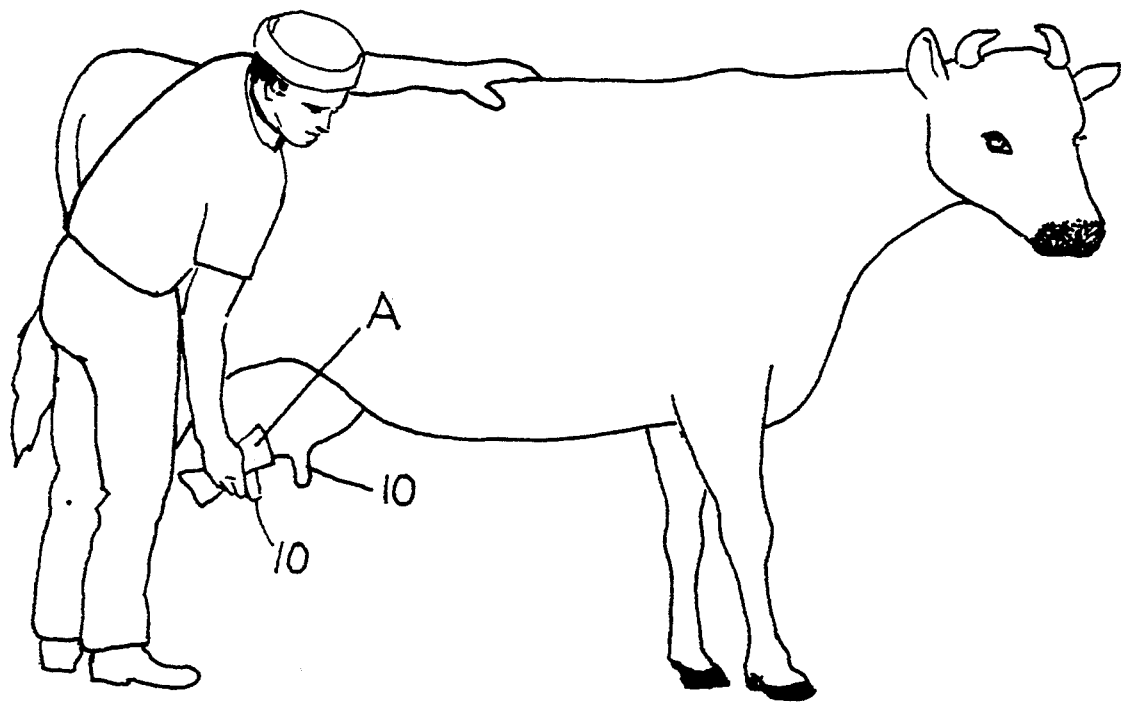
FIG. 3 is a perspective view illustrating the step of manually massaging the teats with the non-woven wipe preparatory to discarding the wipe prior to treating another cow.
Figure 4:
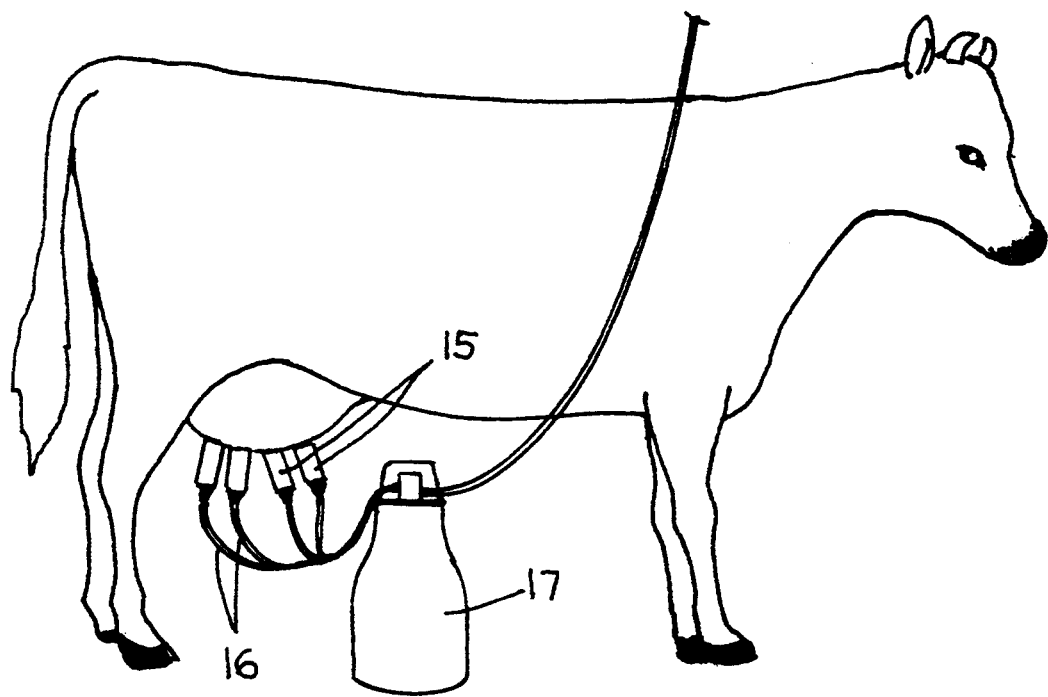
FIG. 4 illustrates milking the cow after receiving the aforesaid treatment.

The drawings illustrate the method wherein the teats 10 and the udder 11 are washed preferably with a solution of soap and water 12 from the nozzle 13. A wipe A is illustrated as being textured as at 12 and consists essentially of a substrate in the form of a binderless non-woven. FIG. 3 illustrates the steps of wrapping the wipe A successively about the teats and manually massaging them until they are dry and releasing the antimicrobial agent which disinfects the teats. FIG. 4 illustrates the milking step which follows massaging which in this embodiment utilizes a milking machine having suction members 15 receiving the teats with respective tubes 16 transporting milk to a collection point 17.

This invention relates to a process for preparing cows for milking comprising the steps of:

1. washing teats and udder of a milk-bearing cow with an aqueous wash such as water or an aqueous soap solution;
2. simultaneously drying, sanitizing and conditioning the thus-washed teats and udder with a moisture-activated antimicrobial wipe comprising a hydrophilic substrate impregnated with an amount of an antimicrobial agent, effective to sanitize the teats and udder; and
3. thereafter milking the thus-prepared cow.

The teats and udders of milk-bearing cows are washed with water or an aqueous soap solution. This may be conveniently accomplished by hosing the teats and udder of cows being prepared by milking for a predetermined period of time, for example, 30–60 sec. This can be carried out in a separate washing area, provided with means for keeping the cows in a desired position with respect to the nozzles of a water or soap dispensing system, after which the cows can be directed into a milking area. Alternatively, the cows can be directed into a milking area and the teats and udder of each cow can be hosed or sprayed with aqueous soap solution from a stationery or mobile source of water or soap solution. It is preferred to wash the teats and udder with aqueous soap solution, the proportions of which can be determined by routine experimentation, in view of instructions provided with commercially-available soap concentrates. It will be understood that soap includes any material commercially formulated for washing teats and udders of milk-bearing cows. A representative product is Novalsan which is made by Ft. Dodge and sold by Team Products of Galesville, Wisconsin, and Babson Bros. Co. of Oak Brook, Illinois.

The teats and udder of each cow are then dried, sanitized and conditioned for milking using an antimicrobial wipe, comprising a hydrophilic substrate, impregnated with an amount of a water-activatable or water-releasable antimicrobial agent, effective to sanitize the teats and udder. The milking attendant simply dries the teats and udder with the impregnated wipe until the teats and udder appear to be dry. Moisture remaining from washing with water or soap solution releases and thereby activates antimicrobial agent in the wipe and the antimicrobial agent is released to reduce the concentration of microorganisms, present on the teats and udder, and thus to sanitize the teats and udder to a level acceptable for milking. Manipulation of the wipe by the milking attendant serves to massage the teats and udder and thereby condition the teats and udder for milking, so as to maximize milk output at each milking. An antimicrobial wipe is normally used for only one cow and is therefore discarded after use.

The wipes can be provided in the form of a roll or napkin, which can be affixed in a permanent location in each stall in a milking area or which can be mounted on a milking cart. The antimicrobial wipes can be dispensed from boxes at any given milking location.

After the teats and udder have been dried, sanitized and conditioned, the milking attendant can, if desired, take samples of milk from each teat. The teat cups of a vacuum milking apparatus are attached to the teats of a thus-prepared milk-bearing cow and connected to a vacuum source when the milking apparatus is applied within 30–60 seconds after being dried with the wipe, the milking apparatus is applied for 5–15 minutes. While milk is flowing for a normal or customary time, the teat cups are then disconnected and the cow is directed out of the milking area. It will be understood that manual milking of a milk-bearing cow can also be carried out.

The process of this invention is advantageous in large or small milking operations because the process eliminates a separate conditioning step and can be carried out by a single attendant. The process requires no elaborate equipment to be installed or maintained.

As is apparent from comparison of Applicant's process with that of the prior art (Table I), Applicant's process allows preparation of cows for milking significantly faster, for example 15 seconds per cow, than conventional preparation processes. Accordingly, labor costs are reduced. In addition, use of the water-activatable wipes to dry and condition the teats and udders of the milk-bearing cow reduces the possibility of cross-contamination, caused by run off from the teat dip, teat spray or water when washing the udder and teats.

The antimicrobial wipes are made from a hydrophilic substrate. The hydrophilic substrate is conveniently characterized by its absorption capacity, which is its ability to take up and retain water. Absorption capacity can be determined as described in U.S. Pat. No. 3,843,395, herein incorporated by reference. Kraft or bond paper has an absorption capacity of about 3.5–4, one-ply, one-ply paper toweling has an absorption capacity of 5–6 and two-ply paper toweling an absorption capacity of 7–9.5.

It has been found that substrates with absorption capacities below about 5 release antimicrobial agent readily, but fail to dry the teats and udder satisfactorily. Hydrophilic substrates, having an absorption capacity above about 12, dry the teats and udder very effectively, but tend to hold the impregnated antimicrobial agent very tenaciously and release insufficient antimicrobial agent to sanitize the teats and udder of a milk-bearing cow. Hydrophilic substrates having absorption capacities from about 5 to about 12 are preferred because wipes having this range of absorption capacities have a balance between ease of release of antimicrobial agent and ability to dry and condition the teats and udder adequately. Suitable hydrophilic materials broadly include sponges, paper and woven-and nonwoven cloth. Representative commercially available substrates include single- and two-ply paper toweling and dryer sheet substrate.

The hydrophilic substrates can be made from natural or synthetic fibers or filaments, particularly wool, silk, jute, hemp, cotton, linen, sisal or ramie among naturally-occurring fibers or rayon, cellulose ester, polyvinyl materials, polyolefins, polyamides, or polyesters, among synthetic fibers, super absorbent fibers and pulp (paper). Any of these materials, or a combination thereof, can be fabricated into adhesively-bonded fibrous or filamentous products, in the form of a web or fibrous mat, in which fibers are distributed randomly or in partially-oriented fashion.

The fibers or filaments in the web or mat can be bonded with adhesives, of which starches, wet-strength resins, vinyl acetate copolymers and ethylene-vinyl acetate are representative.

Substrate selection is markedly influenced by economic factors. At present, a preferred hydrophilic substrate is a non-woven fabric from a blend of rayon and cotton bonded by a copolymer of vinyl acetate with an acrylic ester or ethylene. Non-bonded fibrous webs can also be used.

Super absorbent fibers include, for example, those disclosed as sorbent fibers by Chang et al. U.S. Pat. No. 4,769,022, herein incorporated by reference. A representative super absorbent fiber is an acrylonitrile fiber, on the surface of which is a hydrophilic crosslinked polymer.

The disposable water-activated or water-activatable antimicrobial wipe which simultaneously dries, sanitizes and conditions the teats and udders of milk-bearing cows, immediately prior to milking, scours the teats and udder and thus reduces solid debris in the milk supply.

Useful antimicrobial agents are selected from non-volatile solid materials, which have relatively high antimicrobial activity, relatively low toxicity, relatively low irritation potential and acceptable physical characteristics. The antimicrobial agent selected should not adversely affect the taste or other properties of the milk obtained, including the ability of the milk to clabber. Representative types of antimicrobial agents include, but are not limited to, quaternary ammonium compounds, biguanides, carbanilides, substituted phenols and metal compounds. It will be understood that "antimicrobial agent" and "antimicrobial composition", as used in the specification and claims are synonymous.

Quaternary ammonium compounds include those having one or more quaternary nitrogen atoms, including hydrocarbyl substituted ammonium compounds and compounds wherein a quaternary nitrogen atom is part of a heterocyclic ring. Typical acceptable quaternary hydrocarbyl ammonium compounds are methylbenethonium chloride, benzalkonium chloride, dodecyltrimethyl ammonium bromide, tetradecyltrimethyl ammonium bromide, and hexadecyltrimethyl ammonium bromide. Heterocyclic quaternary ammonium antimicrobial compounds include dodecylpyridinium chloride, tetradecylpyridinium chloride, cetylpyridinium chloride, tetradecyl-4-ethylpyridinium chloride and tetradecyl-4-methylpyridinium chloride.

Other representative compounds include [(diisobutylphenoxy)ethoxy]ethyltrimethyl ammonium chloride, (methyldodecylbenzy)trimethyl ammonium chloride, octadecyldimethylethyl ammonium bromide, octadecenyl-9-dimethylethyl ammonium bromide, N-[acylcolaminoformylmethyl) pyridinium chloride, laurylpyridinium chloride and cetylpyridinium chloride.

Quaternary ammonium antimicrobial agents can be represented the formula $R_1R_2R_3R_4N^+An^-$, wherein $R_1$–$R_4$ are alkyl; any two of $R_1$–$R_4$ together can form an N-heterocyclic ring; at least one of $R_1$–$R_4$ is of 8–30 carbon atoms; one of $R_1$–$R_4$ can be benzyl; and $An^-$ an anion. Anions include chloride, bromide, iodide, sulfate, nitrate, methosulfate and the like.

Preferred quaternary ammonium compounds are quaternary ammonium chlorides, of which benzalkonium chloride is most preferred. Benzalkonium chloride refers to a class of higher alkyldimethylbenzyl ammonium chlorides, or a corresponding mixture. Benzalkonium chloride can be represented by the formula $C_6H_5CH_2N(CH_3)_2N^+R\ Cl^-$, wherein R is alkyl or alkenyl of 8–18 carbon atoms.

Biguanides include bis- and polybiguanides, of which 1,6-bis(4-chlorophenyl)diguanidohexane (chlorhexidine) and its water-soluble salts are preferred. Water-soluble salts of biguanides include the hydrochloride, acetate and gluconate, of which the hydrochloride is preferred.

Representative carbanilides include 3,4,4'-trichlorocarbanilide (triclocarban) and 3- (trifluoromethyl)-4,4'-dichlorocarbanilide.

Substituted phenols include 5-chloro-2-(2,4-dichlorophenoxy) phenol and 2,2'-methylenebis-(3,4,6-trichlorophenol) (hexachlorophene).

Iodophors include, but are not limited to, complexes of iodine with polymers such as poly(vinylpyrrolidone) or polyoxyethylated phenols, as disclosed by Richter, supra.

The hydrophilic substrate is impregnated with antimicrobial agent so that at least some of the antimicrobial agent permeates the structure of the substrate, rather than being coated on the surface alone. The antimicrobial agent can be applied to the hydrophilic substrate by padding, which means that the antimicrobial agent is dissolved or suspended in a liquid carrier and applied to the hydrophilic substrate, using a porous applicator.

A liquid solution or suspension of the antimicrobial agent can be charged to a pan or trough, through which a roll of hydrophilic substrate (absorbent paper or non-woven) is passed at a speed sufficiently slow so that the hydrophilic substrate takes up antimicrobial agent. Excess antimicrobial agent is squeezed from the hydrophilic substrate using rollers and, if necessary, the hydrophilic substrate is dried. Alternatively, a solution or suspension of antimicrobial agent can be sprayed onto the hydrophilic substrate. Any excess is removed by the use of squeeze rollers or a doctor blade.

Rolls of thus-impregnated hydrophilic substrate can be folded, cut or perforated to provide uniform sheets of antimicrobial wipes.

The amount of antimicrobial agent, with which the hydrophilic substrate is impregnated, is from about 0.5% to about 5% by weight of the substrate. Preferably, the level of antimicrobial agent is 1.00% to 2% by weight.

The antimicrobial agent can be applied from water or from an organic solvent. It is preferred to impregnate the substrate with antimicrobial agent from an aqueous solution or suspension.

The milk from cows, whose teats have been treated as above, meets U.S. Government standards for milk products. Specifically, raw milk from cows thus milked does not exceed 100,000 colony forming units/mL, prior to commingling with other producers' milk. Commingled milk should not exceed 300,000 colony forming units/mL before pasteurization [2] C.F.R., §110 (1983)].

BEST MODE FOR CARRYING OUT THE INVENTION

In a most preferred embodiment, the hydrophilic substrate is an apertured non-woven fabric of a pulp blend, bonded by an acrylic-vinyl acetate or ethylene-vinyl acetate copolymers, and the antimicrobial agent is chlorhexidine.

A most preferred level of antimicrobial agent is 1.00% to 2% by weight of the hydrophilic substrate.

Without further elaboration it is believed that one skilled in the art can, using the preceding description, utilize the present invention to its fullest extent. The following preferred specific embodiments are, therefore to be construed as merely illustrative and not limitative of the disclosure in any way whatsoever.

In the following examples, temperatures are set forth uncorrected in degrees Celsius. Unless otherwise indicated, all parts and percentages are by weight.

EXAMPLE 1

Preparation of Wipes Impregnated with Antimicrobial Agents

Dryer sheets (22.86 cm×27.94 cm, made of a rayon blend, bonded with ethylene-vinyl acetate copolymer, absorption capacity 800% are impregnated with antimicrobial agents by dissolving the antimicrobial agent being tested to the ethylene-vinyl acetate binder and saturating the sheets, which are then dried. The uptake of antimicrobial agent is 4% by weight (dry) of the sheet.

Sheets are thus impregnated with the following antimicrobial agents
% by weight: 4% chlorhexidine

EXAMPLE 2

Antimicrobial Efficacy of Impregnated Wipes

Dryer sheets, impregnated as in Example 1, with 4% by weight of chlorhexidine are evaluated for effect on representative organisms, that is Salmonella, *Staph. aureus, Strep. agalactiae, Strep. uberis, Strep. dysgalactiae coliforms,* Pseudomonades, and *Escherichia coli.* The wipe specimens contained the following loadings (% of weight) of antimicrobial agent:

Sheets:
A 4% of chlorhexidine
B without antimicrobial agent control
C without antimicrobial agent control
D without antimicrobial agent control Sterile glass slides are inoculated with the selected organism. Each test sheet is cut in half and moistened. A moistened test sheet is used to wipe each slide ten times. The slides are then incubated in Letheen broth for 2 days at 36° C.

The following results are obtained:

| Specimen | Salmonella, | Staph. Aureus, | Strep. Agalactiae, |
|---|---|---|---|
| A | no growth | no growth | no growth |
| B | growth | growth | growth |
| C | growth | growth | growth |
| D | growth | growth | growth |

| Specimen | Strep. Uberis | Strep. Dysgalactiae | Coliforms |
|---|---|---|---|
| A | no growth | no growth | |
| B | growth | growth | |
| C | growth | growth | |
| D | growth | growth | |

| Specimen | Pseudomonades | Escherichia Coli |
|---|---|---|
| A | no growth | no growth |
| B | growth | growth |
| C | growth | growth |
| D | growth | growth |

EXAMPLE 3

Dermal Irritation Study

Dryer cloth is impregnated with 4% by weight of chlorhexidine and dried. The treated sheets are tested in accordance with 16 C.F.R., Federal Hazardous Substances Act, Ch. II, Subchapter C, 1500.41 (1988).

The skin of six albino rabbits is clipped free of fur. Both intact and abraded skin sites are used for testing. Adjacent areas of untreated skin are used as control sites.

Test samples (2.5×2.5 cm) are applied to the test cites, covered with gauze patches and secured with non-irritating, non-adhesive wrap. The test animals are exposed to the test specimens for 24 h. The test sites are scored for irritation 30 and 60 sec. after removal of the test specimens and at 48 and 72 h. after application. The test sites are scored according to the Draize scale for erythema (redness) and edema (swelling). Scores for erythema and edema at 24 and 72 h. on intact and abraded skin are summed and divided by four to obtain the Primary irritation index for the test application.

None of the test animals exhibited signs of erythema or edema during the 72 h. observation period. The Primary Skin Irritation Index is 0.0 and the test article is not a skin irritant, as defined by 16 C.F.R. 1500.41.

EXAMPLE 4

Use of Wipes Impregnated with Antimicrobial Agents in Milking Cows (a) Wipes are prepared as in Example 1, using 1.5% by weight of chlorhexidine as antimicrobial agent. The wipes are used in the milking barn of a dairy farm. The teats and udders of the cows are first hosed down with an aqueous soap solution. The milking attendant uses an impregnated wipe to dry and massage the teats and udder, as a result of which the teats and udder are dried, sanitized and conditioned for milking. Teat cups of a conventional milking apparatus are applied in the usual manner and the cow is milked. Use of the impregnated wipes does not deleteriously affect the quality or quantity of the milk obtained. The taste and ability of the milk to clabber are unaffected.

(b) Two-layer paper toweling is impregnated with 1.5% by weight of chlorhexidine. The toweling is dried in air. Pieces of impregnated toweling are used as in part (a). Similar results are obtained.

(c) Similar results are obtained, using wipes prepared from non-bonded non-woven fabrics, impregnated with about 1.5% by weight of benzalkonium chloride.

(d) Similar results are obtained, using wipes prepared from apertured non-bonded material, impregnated with about 1.75% by weight of 3,4,4'-trichloroearbanilide.

EXAMPLE 5

Comparative Testing of Wipes

Tests were run on two different days, using four different types of wipes:
1 non-woven fiber towel (Dexter Corp.)
2 paper dairy towel (Scott Paper)
3 non-woven towel, containing 1.5% by weight of chlorhexidine
4 non-woven towel, containing 1.0% by weight of chlorhexidine Each test involved about 64 cows, which entered the milking parlor from freestall barns in groups of eight cows per side. Treatments were alternated between sides of the milking parlor.

Teats were swabbed before the treatment to obtain a bacterial sample from each cow. A towel was wetted for each cow and teats were washed and dried for 15 sec. Teats were swabbed again one min. after treatment to obtain a bacterial sample, after treatment.

Bacterial cultures were grown from material on the swabs, both before and after treatment. The results were analyzed by SAS General Linear models and results (reduction of bacterial count) are presented in the form of least square means:

| Treatment | Reduction of Bacterial Count |
|---|---|
| #1 | 5,720 |
| #2 | 29,768 |
| #3 | 58,940 |
| #4 | 40,798 |

By Tukey's Studentized Range (HSD), comparisons are significant at the 0.05 level. The results show that the reduced bacterial count, obtained using the towel of Example #3, is statistically significant and that use of the moisture-activatable wipes effectively sanitizes the teats and udders of the cows being treated therewith.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

I claim:

1. The method of preparing cows for milking while treating the teats to reduce contamination by reducing the concentration of bacteria of the milk collected consisting of the following steps performed sequentially:
   A. washing the teats of a milk bearing cow by applying water or an aqueous soap solution thereto so as to leave the teats wet therewith;
   B. manually massaging the tests while still wet with a flexible wipe constructed of a hydrophilic material selected from the group consisting of wool, silk, jute, hemp, cotton, linen, sisal, ramie, rayon, cellulose esters, polyvinyl materials, polyolefins, polyamides, polyesters, paper or a combination thereof including about 0.5–5% by weight of a moisture-activated antimicrobial composition selected from the group consisting of biguanides, quaternary ammonium compounds and carbanilides releasable from the wipe by uptake of water;
   C. continuing to manually massage the teats with said wipe after moistening thereof so as to apply said moisture-activated antimicrobial composition released from the wipe to the teats to dry and to sanitize the teats;
   D. discarding said flexible wipe prior to preparing and treating another cow; and
   E. thereupon milking the thus-prepared cow;
   whereby washing and drying of the teats of a cow are accomplished.

2. The method set forth in claim 1, wherein the flexible wipe includes a substrate having an absorption capacity of about 5–12 times its weight of water.

3. The method set forth in claim 1, wherein the flexible wipe includes a substrate comprising a non-woven fabric.

4. The method set forth in claim 1, wherein the flexible wipe includes a substrate comprising a non-woven fabric bonded by a copolymer of vinyl acetate with an acrylic ester or ethylene.

5. The method set forth in claim 1, wherein the flexible wipe contains 1.00%–2% by weight of said antimicrobial composition.

6. The method set forth in claim 1, wherein the antimicrobial composition is chlorhexidine.

7. The method set forth in claim 1, wherein the antimicrobial composition is benzalkonium chloride.

* * * * *

UNITED STATES PATENT AND TRADEMARK OFFICE
CERTIFICATE OF CORRECTION

PATENT NO. : 5,366,732
DATED : November 22, 1994
INVENTOR(S) : Jaime Zighelboim R.

It is certified that error appears in the above-indentified patent and that said Letters Patent is hereby corrected as shown below:

Claim 1, column 9, line 35, "tests" should read --teats--

Signed and Sealed this

Fourteenth Day of February, 1995

Attest:

BRUCE LEHMAN

Attesting Officer     Commissioner of Patents and Trademarks